United States Patent
Xu et al.

(10) Patent No.: US 7,514,260 B2
(45) Date of Patent: Apr. 7, 2009

(54) FEEDER INDEPENDENT EXTENDED CULTURE OF EMBRYONIC STEM CELLS

(75) Inventors: Ren-He Xu, Madison, WI (US); James A. Thomson, Madison, WI (US)

(73) Assignee: WiCell Research Institute, Inc., Madison, WI (US)

( * ) Notice: Subject to any disclaimer, the term of this patent is extended or adjusted under 35 U.S.C. 154(b) by 311 days.

(21) Appl. No.: 11/134,564

(22) Filed: May 20, 2005

(65) Prior Publication Data

US 2006/0014279 A1 Jan. 19, 2006

Related U.S. Application Data

(60) Provisional application No. 60/573,545, filed on May 21, 2004.

(51) Int. Cl.
  *C12N 5/00* (2006.01)
  *C12N 5/02* (2006.01)
  *C12N 5/08* (2006.01)
(52) U.S. Cl. .................................... 435/383; 435/366
(58) Field of Classification Search ................. 435/383, 435/366
See application file for complete search history.

(56) References Cited

U.S. PATENT DOCUMENTS 7,294,510 B2    11/2007  Okano et al.
2003/0017589 A1 * 1/2003  Mandalam et al. .......... 435/366

FOREIGN PATENT DOCUMENTS

WO       WO 01/66697 A2    9/2001

OTHER PUBLICATIONS

Lim et al. Proteomics, 2:1187-1203, 2002.*
Thomson. PNAS, 92: 7844-7848, Aug. 1995.*
DMEM product information. Invitrogen Catalog, accessed online at https://catalog.invitrogen.com/ on Oct. 19, 2007.*
X-Vivo 10 production Information. Lonza Catalog, accessed online at http://www.lonzabioscience.com/Lonza_CatNav.oid.804.prodoid.Xvivo10.*
Bellantuono et al. (One Day Symposium on the use of embryonic stem cells for cell therapy and the Modeling of Human Diseases, accessed online at http://www.isscr.org/science/sheffieldconf.htm, publically available, Dec. 3, 2004.*
Pera, M.F., et al., "Regulation of Human Embryonic Stem Cell Differentiation by BMP-2 and its Antagonist Noggin," Journal of Cell Science 117:1269-1280 (2003).
Amit, M., et al., "Human Feeder Layers for Human Embryonic Stem Cells," Biology of Reproduction 68:2150-2156 (2003).
Amit, M., et al., "Feeder Layer- and Serum-Free Culture of Human Embryonic Stem Cells," Biology of Reproduction 70:837-845 (2004).
Richards, M., et al., "Human feeders support prolonged undifferentiated growth of human inner cell masses and embryonic stem cells," Nature Biotechnology 20:933-936 (2002).
Wang, G., et al., "Noggin and bFGF cooperate to maintain the pluripotency of human embryonic stem cells in the absence of feeder layers," Biochemical and Biophysical Research Communications 330:934-942 (2005).
Xu, C., et al., "Feeder-free growth of undifferentiated human embryonic stem cells," Nature Biotechnology 19:971-974 (2001).
Xu, R., et al., "BMP4 initiates human embryonic stem cell differentiation to trophoblast," Nature Biotechnology 20:1261-1264 (2002).
Xu, R., et al., "Basic FGF and suppression of BMP signaling sustain undifferentiated proliferation of uman ES cells," Nature Methods 2:185-190 (2005).
U.S. Appl. No. 60/552,318, filed Mar. 10, 2004, Beattie, et al., Provisional Appln. filed Mar. 10, 2004.

* cited by examiner

*Primary Examiner*—Thaian N Ton
(74) *Attorney, Agent, or Firm*—Quarles & Brady LLP

(57) ABSTRACT

Previous methods for culturing human embryonic stem cells have required either fibroblast feeder cells or a medium which has been exposed to fibroblast feeder cells in order to maintain the stem cells in an undifferentiated state. It has now been found that if an antagonist of bone morphogenic protein is added to the medium in which the stem cells are cultured, together with fibroblast growth factor, the stem cells will remain undifferentiated indefinitely, even without feeder cells or conditioned medium.

9 Claims, No Drawings

SEQUENCE LISTING

<160> NUMBER OF SEQ ID NOS: 28

<210> SEQ ID NO 1
<211> LENGTH: 19
<212> TYPE: DNA
<213> ORGANISM: Artificial
<220> FEATURE:
<223> OTHER INFORMATION: Synthetic PCR Primer

<400> SEQUENCE: 1
ggtgcgctgt ctgtctgag                                              19

<210> SEQ ID NO 2
<211> LENGTH: 18
<212> TYPE: DNA
<213> ORGANISM: Artificial
<220> FEATURE:
<223> OTHER INFORMATION: Synthetic PCR Primer

<400> SEQUENCE: 2
ctgatctcgc cgttgagg                                               18

<210> SEQ ID NO 3
<211> LENGTH: 20
<212> TYPE: DNA
<213> ORGANISM: Artificial
<220> FEATURE:
<223> OTHER INFORMATION: Synthetic PCR Primer

<400> SEQUENCE: 3
gcagcacctc atcgactaca                                             20

-continued

<210> SEQ ID NO 4
<211> LENGTH: 20
<212> TYPE: DNA
<213> ORGANISM: Artificial
<220> FEATURE:
<223> OTHER INFORMATION: Synthetic PCR Primer

<400> SEQUENCE: 4
aattcagaag cctgcaagga                                          20

<210> SEQ ID NO 5
<211> LENGTH: 20
<212> TYPE: DNA
<213> ORGANISM: Artificial
<220> FEATURE:
<223> OTHER INFORMATION: Synthetic PCR Primer

<400> SEQUENCE: 5
ctggacgaca tgaaccactg                                          20

<210> SEQ ID NO 6
<211> LENGTH: 20
<212> TYPE: DNA
<213> ORGANISM: Artificial
<220> FEATURE:
<223> OTHER INFORMATION: Synthetic PCR Primer

<400> SEQUENCE: 6
gtagtcgatg acgcgctgta                                          20

<210> SEQ ID NO 7
<211> LENGTH: 25
<212> TYPE: DNA
<213> ORGANISM: Artificial
<220> FEATURE:
<223> OTHER INFORMATION: Synthetic PCR Primer

<400> SEQUENCE: 7
atgaaggcgg tgagcccggt gcgcc                                    25

<210> SEQ ID NO 8
<211> LENGTH: 25
<212> TYPE: DNA
<213> ORGANISM: Artificial
<220> FEATURE:
<223> OTHER INFORMATION: Synthetic PCR Primer

<400> SEQUENCE: 8
tgtggccgtg ctcggccagg cagcg                                    25

<210> SEQ ID NO 9
<211> LENGTH: 20
<212> TYPE: DNA
<213> ORGANISM: Artificial
<220> FEATURE:
<223> OTHER INFORMATION: Synthetic PCR Primer

<400> SEQUENCE: 9
gagtccactg gcgtcttcac                                          20

<210> SEQ ID NO 10
<211> LENGTH: 20
<212> TYPE: DNA
<213> ORGANISM: Artificial
<220> FEATURE:

```
<223> OTHER INFORMATION: Synthetic PCR Primer

<400> SEQUENCE: 10
ctcagtgtag cccaggatgc                                                     20

<210> SEQ ID NO 11
<211> LENGTH: 21
<212> TYPE: DNA
<213> ORGANISM: Artificial
<220> FEATURE:
<223> OTHER INFORMATION: Synthetic PCR Primer

<400> SEQUENCE: 11
gggaaggtat tcagccaaac g                                                   21

<210> SEQ ID NO 12
<211> LENGTH: 20
<212> TYPE: DNA
<213> ORGANISM: Artificial
<220> FEATURE:
<223> OTHER INFORMATION: Synthetic PCR Primer

<400> SEQUENCE: 12
ggttcgcttt ctctttcggg                                                     20

<210> SEQ ID NO 13
<211> LENGTH: 23
<212> TYPE: DNA
<213> ORGANISM: Artificial
<220> FEATURE:
<223> OTHER INFORMATION: Synthetic PCR Primer

<400> SEQUENCE: 13
aatacctcag cctccagcag atg                                                 23

<210> SEQ ID NO 14
<211> LENGTH: 22
<212> TYPE: DNA
<213> ORGANISM: Artificial
<220> FEATURE:
<223> OTHER INFORMATION: Synthetic PCR Primer

<400> SEQUENCE: 14
caaagcagcc tccaagtcac tg                                                  22

<210> SEQ ID NO 15
<211> LENGTH: 22
<212> TYPE: DNA
<213> ORGANISM: Artificial
<220> FEATURE:
<223> OTHER INFORMATION: Synthetic PCR Primer

<400> SEQUENCE: 15
cctggaggaa tacctggcat tg                                                  22

<210> SEQ ID NO 16
<211> LENGTH: 20
<212> TYPE: DNA
<213> ORGANISM: Artificial
<220> FEATURE:
<223> OTHER INFORMATION: Synthetic PCR Primer

<400> SEQUENCE: 16
tctgaggaca agcgattgcg                                                     20
```

```
<210> SEQ ID NO 17
<211> LENGTH: 24
<212> TYPE: DNA
<213> ORGANISM: Artificial
<220> FEATURE:
<223> OTHER INFORMATION: Synthetic PCR Primer

<400> SEQUENCE: 17
tgagatcact tcaccgtggt ctcc                                              24

<210> SEQ ID NO 18
<211> LENGTH: 22
<212> TYPE: DNA
<213> ORGANISM: Artificial
<220> FEATURE:
<223> OTHER INFORMATION: Synthetic PCR Primer

<400> SEQUENCE: 18
tttatacctc ggggttgtgg gg                                                22

<210> SEQ ID NO 19
<211> LENGTH: 23
<212> TYPE: DNA
<213> ORGANISM: Artificial
<220> FEATURE:
<223> OTHER INFORMATION: Synthetic PCR Primer

<400> SEQUENCE: 19
cgtccatctt tgcttgggaa atc                                               23

<210> SEQ ID NO 20
<211> LENGTH: 23
<212> TYPE: DNA
<213> ORGANISM: Artificial
<220> FEATURE:
<223> OTHER INFORMATION: Synthetic PCR Primer

<400> SEQUENCE: 20
gagcctcatc tgaatcttct ccg                                               23

<210> SEQ ID NO 21
<211> LENGTH: 24
<212> TYPE: DNA
<213> ORGANISM: Artificial
<220> FEATURE:
<223> OTHER INFORMATION: Synthetic PCR Primer

<400> SEQUENCE: 21
aagccatgaa cgcagaggag gact                                              24

<210> SEQ ID NO 22
<211> LENGTH: 20
<212> TYPE: DNA
<213> ORGANISM: Artificial
<220> FEATURE:
<223> OTHER INFORMATION: Synthetic PCR Primer

<400> SEQUENCE: 22
agctgtccat ggtaccgtaa                                                   20

<210> SEQ ID NO 23
<211> LENGTH: 24
<212> TYPE: DNA
<213> ORGANISM: Artificial
<220> FEATURE:
<223> OTHER INFORMATION: Synthetic PCR Primer
```

-continued

```
<400> SEQUENCE: 23
aacccaactg tggagatgat gcag                                              24

<210> SEQ ID NO 24
<211> LENGTH: 24
<212> TYPE: DNA
<213> ORGANISM: Artificial
<220> FEATURE:
<223> OTHER INFORMATION: Synthetic PCR Primer

<400> SEQUENCE: 24
aggggcttca ctaataactg gacg                                              24

<210> SEQ ID NO 25
<211> LENGTH: 21
<212> TYPE: DNA
<213> ORGANISM: Artificial
<220> FEATURE:
<223> OTHER INFORMATION: Synthetic PCR Primer

<400> SEQUENCE: 25
ccaagccgcc ttactcctac a                                                 21

<210> SEQ ID NO 26
<211> LENGTH: 21
<212> TYPE: DNA
<213> ORGANISM: Artificial
<220> FEATURE:
<223> OTHER INFORMATION: Synthetic PCR Primer

<400> SEQUENCE: 26
cgcagatgaa gacgctggag a                                                 21

<210> SEQ ID NO 27
<211> LENGTH: 25
<212> TYPE: DNA
<213> ORGANISM: Artificial
<220> FEATURE:
<223> OTHER INFORMATION: Synthetic PCR Primer

<400> SEQUENCE: 27
tggcaccaca ccttctacaa tgagc                                             25

<210> SEQ ID NO 28
<211> LENGTH: 25
<212> TYPE: DNA
<213> ORGANISM: Artificial
<220> FEATURE:
<223> OTHER INFORMATION: Synthetic PCR Primer

<400> SEQUENCE: 28
gcacagcttc tccttaatgt cacgc                                             25
```

FEEDER INDEPENDENT EXTENDED CULTURE OF EMBRYONIC STEM CELLS

CROSS-REFERENCE TO RELATED APPLICATIONS

This application claims priority from U.S. provisional patent application Ser. No. 60/573,545 filed May 21, 2004.

STATEMENT REGARDING FEDERALLY SPONSORED RESEARCH OR DEVELOPMENT

To be determined.

BACKGROUND OF THE INVENTION

Stem cells are defined as cells that are capable of a differentiation into many other differentiated cell types. Embryonic stem cells are stem cells from embryos which are capable of differentiation into most, if not all, of the differentiated cell types of a mature body. Stem cells are referred to as pluripotent, which describes this capability of differentiating into many cell types. A category of pluripotent stem cell of high interest to the research community is the human embryonic stem cell, abbreviated here as hES cell, which is an embryonic stem cell derived from a human embryonic source. Human embryonic stem cells are of great scientific interest because they are capable of indefinite proliferation in culture and are thus capable, at least in principle, of supplying cells and tissues for replacement of failing or defective human tissue. The existence in culture of human embryonic stem cells offers the potential of unlimited amounts of human cells and tissues for use in a variety of therapeutic protocols to assist in human health. It is envisioned in the future human embryonic stem cells will be proliferated and directed to differentiate into specific lineages so as to develop differentiated cells or tissues which can be transplanted into human bodies for therapeutic purposes.

One of most significant features of human embryonic stem cells is the attribute of being capable of self-renewal. By that, it is meant that the hES cells are capable of proliferating into multiple progeny stem cells, each of which seems to have the full potential of its ancestor cell. In other words, the progeny are renewed to have all the developmental and proliferative capacity of the parental cell. This attribute, combined with the pluripotency, are the traits that make hES cells candidates for many potential uses, since, the theory, hES cells can be reproduced indefinitely and in large numbers and then induced to become any cell type in the human body. The attribute of ability to self-renew appears closely linked to the attribute of being undifferentiated in the sense that at least given present knowledge, only undifferentiated hES cells are capable of indefinite self-renewal and as soon as the cells differentiate, the attribute of self-renewal capability is lost. Since human embryonic stem cells will spontaneously differentiate, care must be taken in culture conditions to maintain the cells in an undifferentiated state.

Basic techniques to create and culture human embryonic stem cells to maintain the cells in an undifferentiated state have been described. The existing techniques do work, but there are limitations and drawbacks to some of the procedures currently used to culture human embryonic stem cells. One limitation is of particular concern. Most existing human embryonic stem cell lines have been, to one degree or another, exposed directly to mouse cells or to a medium in which mouse cells have been cultured previously. The original techniques for the generation and culture of human embryonic stem cells described the use of mouse embryonic fibroblast (MEF) feeder cells as a feeder layer on which human embryonic stem cells could be cultured. The fibroblast feeder layer acts, through some as yet incompletely understood mechanism, to enable the stem cells to remain in an undifferentiated state. Later, it was discovered that the same phenomenon could be achieved if the stem cells were exposed to "conditioned media." A conditioned medium is nothing more than the stem cell culture medium which had previously been cultured on feeder cells such as MEF. Either the feeder cells impart some factor to the medium or remove some factor from the medium, but the result is that the conditioned medium can be used to culture stem cells without differentiation. Either culture condition, the direct growth on feeder cells, or the use of condition media, raises the concern that one or more agents such as a virus could transmit from the mouse cells to the human ES cells. If one of the objectives of human embryonic stem cell cultures is to create tissues which can ultimately be transplanted into a human body, it is highly desirable that the stem cells never have been exposed to cells of another species or to media which have been used to culture cells of another species. Also, the need for feeder cells of any species represents an unneeded biological variable in the culture of stem cells that is best avoided if possible. Accordingly, defining a culture condition, which will permit the proliferation and culture of human embryonic stem cells without a fibroblast feeder layer and without conditioned medium, is of great interest in the continued development of techniques for the use of human embryonic stem cells.

Several medium formulations will permit human ES cells to remain undifferentiated for some time, but that state often fails to maintain itself over long term culture. In particular, we define a passage as the growth of human ES cells from an initial seed culture in a culture plate to growth to cell confluence in the same culture plate as a "passage." We have found several medium formulations that permit the cultivation of human ES cells for one or two passages without severe differentiation, but then the cells differentiate gradually or rapidly upon subsequent passages. We have come to believe that in order for a medium to truly support the indefinite proliferation of human ES cells without differentiation, without feeder cells or feeder conditioned medium, the medium must be demonstrated to support culture of human ES cells in a substantially uniform and undifferentiated state for at least five passages.

BRIEF SUMMARY OF THE INVENTION

The present invention is summarized as a method for culturing human embryonic stem cells without the need for feeder cells or conditioned medium of any kind, the method including the step of culturing the human embryonic stem cells in a medium including salts, vitamins, amino acids, glucose, a fibroblast growth factor and a bone morphogenic protein antagonist in sufficient amount to maintain the stem cells in an undifferentiated state.

The present invention is also directed to an in vitro cell culture of human embryonic stem cells cultured in a medium including a bone morphogenic protein antagonist so that the stem cells can be cultured indefinitely in an undifferentiated state without the need for fibroblast feeder cells or conditioned medium.

It is an object of the present invention to define long term culture conditions for human embryonic stem cells that avoid the use of feeder cells, including both culture on feeder cells and culture in feeder-conditioned medium.

It is another object of the present invention to define culture conditions for human embryonic stem cells that are as defined as possible while being completely independent of feeder cells.

Other objects, features and advantages of the present invention will become apparent from the following specification.

BRIEF DESCRIPTION OF THE SEVERAL VIEWS OF THE DRAWINGS

Not applicable.

DETAILED DESCRIPTION OF THE INVENTION

The observation that human embryonic stem (ES) cell cultures have previously been maintained in an undifferentiated state only when cultured in the presence of fibroblast feeder cells or in conditioned medium has led to speculation that the fibroblasts release into the medium a factor which acts to inhibit differentiation of the ES cells. This speculation is also based on the parallel observations of murine ES cell lines, which, when cultured with fibroblast feeder cells, respond to leukemia inhibitory factor (LIF) secreted by the fibroblasts to remain undifferentiated. The LIF activates a signal pathway in the murine ES cells that triggers self-renewal. However, human ES cells are unresponsive to LIF and indeed do not seem to possess LIF receptors on their cell surface. Since no single factor has been isolated from conditioned medium that seemed to cause the effect of preventing differentiation in human ES cells, we developed a new hypothesis. We hypothesized that instead the fibroblast cells inactivate differentiation factors present in unconditioned medium.

Various research groups have investigated factors that initiate differentiation of human ES cells into progeny cell cultures that are enriched in cells of one or more particular lineage. One of these differentiation factors is a category of protein factor known as bone morphogenic protein (BMP). BMPs are members of the transforming growth factor-β (TGFβ) superfamily of secreted signaling molecules. They play an extensive role in almost all aspects of embryonic development. BMP 4 and other BMP family members, such as BMP2, -5, and -7, bind BMP type II receptor BRII, which recruits type I receptor BR1A (ALK3) or BR1B. Upon ligand activation, the intracellular kinase domain of the type I receptors phosphorylates Smad1, -5, and -8, which are then escorted by a common Smad to enter the nucleus and activate target genes. The relative expression level of BMPs, receptors, and Smads within the cell is an important determinant of BMP-induced responses. Co-stimulation of other signaling pathways also alters the nature of BMP effect. A typical example is the change of BMP action by a co-activated LIF signal in mouse ES cells: BMP signal alone induces non-neural epithelial differentiation, whereas BMP and LIF signals together inhibit differentiation to any lineage. The extracellular BMP antagonists such as noggin, gremlin, chordin, inhibin, follistatin, twisted gastrulation and members of the DAN family, etc. can modify, diminish or totally nullify BMP activities. On the other hand, some signaling pathways can interrupt the BMP signaling intracellularly. For example, the MAPK signaling activated by fibroblast growth factor (FGF) can inhibit the BMP signaling by preventing the Smads from nuclear translocation via phosphorylation of the linker domain of the Smads. Activation of the transforming growth factor beta (TGFβ), Nodal, or Activin signaling pathways may antagonize the BMP signaling via intracellular cross-talk, such as competition for Smad4 to enter the nucleus. It is anticipated that all of these molecules can be used to antagonize BMP signaling to achieve the effects reported here.

It was also observed that the levels of bone morphogenic protein (BMP) stimulated intracellular signal is low is human ES cells grown in conditioned medium, whereas the level of this same signal is high in human ES cells grown out in unconditioned medium (and without fibroblast feeder cells). Perhaps the effect of the conditioning of the medium was due to inhibition of the effects of BMP inducing signals present in the unconditioned medium. We therefore explored the possibility that antagonists of BMP activity could act to enable the cultivation of human ES cells in culture and in an undifferentiated state without the need for feeder cells or conditioned medium. It was discovered, and is reported here, that this possibility was found to be correct. By antagonizing the activity of BMP, it has become possible to culture human ES cells indefinitely, while the cells retain all of the identifying characteristics of embryonic stem cells.

There are a number of antagonists of BMP that can be used in this invention. The most potent known such antagonist is the protein noggin. Other proteins known to function as antagonists of BMPs include gremlin, chordin, inhibin, follistatin, twisted gastrulation and members of the DAN family. As mentioned above, other proteins include TFGP and activin and other molecules which activate the signaling pathway for MAPK. It is not required that the antagonist protein be the human form of the protein. It is only required that it be effective in culture to allow unconditioned medium to maintain ES cells without differentiation. It is also possible to use as an antagonist antibodies specific to all BMPs or a specific BMP. The particular protein chosen as the BMP antagonist is less important than that the desired effect is achieved in that BMP signaling activity is inhibited by the molecule added to the medium. The simplest and most straightforward way to accomplish this is to add the BMP antagonist to the medium in which the human ES cells are cultured.

The most potent BMP inhibitor identified so far, the protein noggin, was originally cloned based on its dorsalizing activity in *Xenopus* embryos. Mouse noggin cDNA encodes a 232 amino acid (aa) residue precursor protein with 19 aa residue putative signal peptide that is cleaved to generate the 213 aa residue mature protein which is secreted as a homodimeric glycoprotein. Noggin is a highly conserved molecule. Mature mouse noggin shares 99% and 83% aa sequence identity with human and *Xenopus* noggin, respectively. Noggin has a complex pattern of expression during embryogenesis. In the adult, noggin is expressed in the central nervous system and in several adult peripheral tissues such as lung, skeletal muscle and skin. Noggin has been shown to be a high-affinity BMP binding protein that antagonizes almost all BMP bioactivities.

It has also been found that high levels of fibroblast growth factor (FGF) are also useful in the culture of stem cells with or without conditioned medium. While it has been previously reported that the addition of FGF is a useful additive to stem cell culture conditions, as in WO 01/66697, in that work, the FGF in the medium in the work reported was basic FGF (bFGF or FGF2) at concentration of 4 ng/ml. Here it is reported that culture with FGF at levels approximately ten-fold higher produces better results. The preferred concentration of bFGF in the work reported here is 40 ng/ml. While others of the various FGF variants also work for this purpose, the concentrations of other FGFs would need to be adjusted to correspond to the efficacy of this level of bFGF, which has been shown by us to also inhibit the intracellular BMP activity.

There appears to be a synergistic relationship between the effect caused by a BMP antagonist and that caused by high levels of FGF in the culture medium. In other words, the use of a high level of bFGF, e.g. at 100 ng/ml, will support cultures of hES cells in an undifferentiated state without feeder cells or conditioned medium, but so will a lesser level of bFGF, e.g. 40 ng/ml when combined with the use of a BMP antagonist such as noggin. Either combination makes the culture not just "feeder free", which is a term used for cultures which make use of conditioned medium (conditioned with feeder cells) but completely "feeder independent," meaning entirely independent of the need for feeder cells of any kind at all.

As the date presented below will demonstrate, this hypothesis has proven to be correct. By adding noggin, or other inhibitor of BMP signaling, and by stimulating the fibroblast growth factor (FGF) signal, human ES cells can be grown indefinitely in an undifferentiated state without either feeder cells or conditioned medium. This permits a human ES cell culture to be initiated and maintained without exposure to feeder cells or medium exposed to feeder cells, thus enabling animal cell-free proliferation of human ES cell lines in a well defined medium.

A related concern in the culture of human ES cells is to remove, to the extent possible, undefined constituents and constituents of animal origin from ES cell culture conditions. This is done for two reasons. One reason is to standardize culture conditions so as to minimize the normal variations in biological materials to the extent possible. The other objective is to avoid the use of materials, cells, exudates or constituents of animal origin so as to avoid any possible cross-species viral transmission through the culture system. Thus it is an objective to define a culture condition that avoids the use of products of animal origin.

So a defined medium for human ES cells begins with a basal medium containing salts, vitamins, glucose and amino acids. The basal medium can be any of a number of commercially available media. We prefer combination of Dulbecco's Modified Eagle Medium and Hams F12 medium, sold as a combination (DMEM/F12). To that basal medium is added glutamine, β-mercaptoethanol, and non-essential amino acids. Other possible additives include antioxidants and lipids. A protein constituent of the medium is a serum substitute product. Albumin or purified albumin products, like the commercial product AlbuMax™, will work, but we prefer a defined protein product made up of albumin, insulin and transferrin. Human proteins are preferred but not essential so long as uncharacterized animal products are excluded.

It is worthy of mention that the observations here indicate a fundamental difference between the mechanisms of self-renewal among stem cells of mammalian species. The conditions which support the maintenance of murine stem cells, including the addition of LIF and BMP to the medium, are insufficient to maintain hES cells in an undifferentiated state. We have been unable to maintain undifferentiated hES cells in serum-free medium supplemented with LIF and BMP4. BMPs cause human ES cells to differentiate into trophoblast cells. In fact, the data presented here teach that BMP signaling must be antagonized to foster human stem cell self-renewal. Thus it is clear that, at a minimum, the cellular mechanisms for self-renewal are very different between the mouse and human cell systems.

EXAMPLES

Methods and Materials

Media and cell culture. Unconditioned medium (UM) contained 80% DMEM/F12 and 20% KNOCKOUT serum replacement, and was supplemented with 1 mM L-glutamine, 1% Nonessential Amino Acids (all from Invitrogen), and 0.1 mM β-mercaptoethanol (Sigma). Conditioned medium (CM) is prepared by incubating unconditioned medium with mouse embryonic fibroblasts overnight and collecting the medium afterwards, which is then supplemented with 4 ng/ml bFGF and refrigerated to be used within 2 weeks. hESCs were cultured on plates coated with Matrigel (BD Scientific) in CM or UM with or without either 0.5 µg/ml mouse noggin (R&D Systems), or 40 ng/ml human bFGF (Invitrogen), or both, and propagated by using 2 mg/ml Dispase (Invitrogen) to loosen the cell colonies. For evaluation of Oct4$^+$ cell number, suspended colonies containing 35,000 cells were added to each medium in multiple wells and cultured for 7 days. Cells were harvested and counted on days 1 and 7, and Oct4$^+$ cells on day 7 were detected by fluorescence-activated cell sorting (FACS, see below). Embryoid bodies (Ebs) were formed by suspending hESCs that had been cultured in CM or UM/bFGF/noggin (UMFN), as cell clumps in UM on a non-coated plate, and culturing them on a rocker for 7 days. The EB cells were then re-plated in DMEM medium supplemented with 10% fetal bovine serum on gelatin-coated plate and cultured for 5 days followed by harvesting and reverse transcription-PCR (RT-PCR) analysis. Experiments were repeated multiple times and ANOVA was used for statistic analysis throughout the studies.

Immunoprecipitation and western blotting. 15 ml of DMEM/F12 medium was conditioned on $2.12 \times 10^5$/ml irradiated mouse embryonic fibroblast cells in a T75 flask overnight. The medium was collected and concentrated to about 0.7 ml with a 5 kD molecular weight cut-off filter (Millipore) and immunoprecipiated with goat anti-mouse noggin and gremlin antibodies (R&D Systems) (5 µg each) or 10 µg goat IgG as a negative control. The precipitated proteins or cell lysates (FIG. 2A) were electrophoresized on a 4%-20% linear gradient Polyacrylamide Tris-HCl Precast Gel (BioRad) for western blotting. The antibodies against mouse noggin and gremlin were used for the immunoprecipitated proteins, and antibodies against human Smad1/5/8, phosphorylated Smad1/5/8 (Cell Signaling Technology), BMP2/4 (R&D Systems), and β-Actin (Abcam) were used for the cell lysates. The blots were treated with the ECL substitute solutions 1 and 2 (Amersham Biosciences) and exposed in a Fuji Imager for chemiluminescence.

BMP/Smad-Luciferase Reporter Assay. hESCs cultured in CM were transfected with a BMP/Smad-responsive firefly luciferase reporter plasmid, pID120-Lux, together with trace amount of pRL-tk plasmid (Promega) to express *Renilla* luciferase as an internal control. One day post-transfection, the cells were treated variously for 24 h. Cell lysates were extracted and both the firefly and *Renilla* luciferase activities tested by using the Dual-Luciferase Reporter Assay System (Promega) on a 3010 Luminometer (BD Biosciences). Results were recorded as the firefly luciferase activity normalized by the *Renilla* luciferase activity.

Quantitative-PCR and RT-PCR. Total cellular RNA was extracted by RNeasy kit (Qiagen), and treated with RNase-free DNase according to the manufacturer's instructions. One µg RNA was reverse transcribed to cDNA with Improm-II Reverse Transcription System (Promega). Quantitative-PCR was performed by using the SYBR green Q-PCR Mastermix (Stratagene) on the AB 7500 Real Time PCR System (Applied Biosystems) under the following conditions: 10 min at 95° C., 40 cycles of 30 sec at 95° C., 1 min at 60° C., and 1 min at 72° C., and 3 min extension at 72° C. GAPDH transcript was tested as an endogenous reference to calculate the relative expression levels of target genes according to Applied Biosystems' instructions. For RT-PCR, following conditions were used: 3 min at 94° C., various cycles (see below) of 20 sec at 94° C., 30 sec at 55° C., and 1 min at 72° C. The PCR reactions were separated on gel by electrophoresis and the DNA bands were visualized under ultraviolet light for photography. The primer sequences and PCR cycle numbers are listed below.

TABLE 1

Primers and cycle numbers for Q-PCR and RT-PCR

| Gene Name | Test | Forward Primer/Reverse Primer | SEQ ID NO: | PCR Cycle # |
|---|---|---|---|---|
| Id1 | Q-PCR | Forward Primer 5'-GGT GCG CTG TCT GTC TGA G | (SEQ ID NO: 1) | 40 |
| | | Reverse Primer 5'-CTG ATC TCG CCG TTG AGG | (SEQ ID NO: 2) | |
| Id2 | Q-PCR | Forward Primer 5'-GCA GCA CCT CAT CGA CTA CA | (SEQ ID NO: 3) | 40 |
| | | Reverse Primer 5'-AAT TCA GAA GCC TGC AAG GA | (SEQ ID NO: 4) | |
| Id3 | Q-PCR | Forward Primer 5'-CTG GAC GAC ATG AAC CAC TG | (SEQ ID NO: 5) | 40 |
| | | Reverse Primer 5'-GTA GTC GAT GAC GCG CTG TA | (SEQ ID NO: 6) | |
| Id4 | Q-PCR | Forward Primer 5'-ATG AAG GCG GTG AGC CCG GTG CGC C | (SEQ ID NO: 7) | 40 |
| | | Reverse Primer 5'-TGT GGC CGT GCT CGG CCA GGC AGC G | (SEQ ID NO: 8) | |
| GAPDH | Q-PCR | Forward Primer 5'-GAG TCC ACT GGC GTC TTC AC | (SEQ ID NO: 9) | 40 |
| | | Reverse Primer 5'-CTC AGT GTA GCC CAG GAT GC | (SEQ ID NO: 10) | |
| Oct4 | RT-PCR | Forward Primer 5'-GGG AAG GTA TTC AGC CAA ACG | (SEQ ID NO: 11) | 35 |
| | | Reverse Primer 5'-GGT TCG CTT TCT CTT TCG GG | (SEQ ID NO: 12) | |
| Nanog | RT-PCR | Forward Primer 5'-AAT ACC TCA GCC TCC AGC AGA TG | (SEQ ID NO: 13) | 35 |
| | | Reverse Primer 5'-CAA AGC AGC CTC CAA GTC ACT G | (SEQ ID NO: 14) | |
| Rex1 | RT-PCR | Forward Primer 5'-CCT GGA GGA ATA CCT GGC ATT G | (SEQ ID NO: 15) | 35 |
| | | Reverse Primer 5'-TCT GAG GAC AAG CGA TTG CG | (SEQ ID NO: 16) | |
| CGβ | RT-PCR | Forward Primer 5'-TGA GAT CAC TTC ACC GTG GTC TCC | (SEQ ID NO: 17) | 30 |
| | | Reverse Primer 5,-TTT ATA CCT CGG GGT TGT GGG G | (SEQ ID NO: 18) | |
| Pax6 | RT-PCR | Forward Primer 5'-CGT CCA TCT TTG CTT GGG AAA TC | (SEQ ID NO: 19) | 30 |
| | | Reverse Primer 5'-GAG CCT CAT CTG AAT CTT CTC CG | (SEQ ID NO: 20) | |
| NeuroD1 | RT-PGR | Forward Primer 5'-AAG CCA TGA ACG CAG AGG AGG ACT | (SEQ ID NO: 21) | 30 |
| | | Reverse Prime 5'-AGG TGT CCA TGG TAC CGT AA | (SEQ ID NO: 22) | |
| Brachyury | RT-PGR | Forward Primer 5'-AAG CCA ACT GTG GAG ATG ATG CAG | (SEQ ID NO: 23) | 35 |
| | | Reverse Primer 5'-AGG GGC TTG ACT AAT AAG TGG AGG | (SEQ ID NO: 24) | |
| HNF3α | RT-PGR | Forward Primer 5'-CCA AGC CGC CTT ACT CCT ACA | (SEQ ID NO: 25) | 30 |
| | | Reverse Primer 5'-CGC AGA TGA AGA CGC TGG AGA | (SEQ ID NO: 26) | |
| B-Actin | RT-PGR | Forward Primer 5'-TGG CAC CAC ACC TTC TAC AAT GAG C | (SEQ ID NO: 27) | 25 |
| | | Reverse Primer 5'-GCA CAG CTT CTC GTT AAT GTC ACG C | (SEQ ID NO: 28) | |

FACS and immunocytochemistry. hESCs cultured in various media were processed for FACS analysis to detect Oct4$^+$ cells. Mouse anti-human Oct4 antibody (Santa Cruz Biotechnology) at 2 μg/ml and fluorescent isothiocyanate-labeled rabbit anti-mouse secondary antibody (Molecular Probes) at 1:1000 dilution were used. Statistic analysis was performed on Arcsine numbers converted from the percentages of Oct4$^+$ cells. For immunocytochemistry, the mouse anti-Oct4 antibody (at 0.2 µg/ml) was used and followed by Alexa Fluor 488-labeled anti-mouse IgG secondary antibody (Molecular Probes) at 1:1000 dilution.

Immunoassay of HCG in the culture medium. hESCs cultured in UMFN (unconditioned medium with bFGF and noggin) for multiple passages were subsequently cultured in CM plus 100 ng/ml BMP4 up to 7 days with daily refreshment of the medium and BMP4. The spent media were collected on days 3, 5, and 7, and assayed for HCG as described.

G-banding and fluorescence in situ hybridization. hESCs cultured in UMFN for various passages were processed for G-banding and fluorescence in situ hybridization. From all the dispersed and fixed cells, 20 cells at metaphase were analyzed for G-banding, and 100-200 nuclei were assayed for fluorescence in situ hybridization using probes to detect marker genes in chromosomes of interest. Representative images captured by the CytoVysion® digital imaging system (Applied Imaging) were reviewed.

Results

UM contains BMP-like differentiation-inducing activity. UM contained 20% KNOCKOUT™ serum replacement (Invitrogen), which includes a proprietary lipid-rich bovine albumin component, ALBUMAX™. UM was conditioned on fibroblasts overnight and then supplemented with 4 ng/ml human bFGF to obtain CM. We cultured hESCs (H1) in CM, UM, a 1:1 mixture of CM with UM, or a 1:1 mixture of CM with DMEM/F 12. The cells in CM or the 1:1 CM-DMEM/F12 mixture remained undifferentiated, and were characterized by typical hESC morphology. However, the cells in UM or the 1:1 CM-UM mixture both rapidly differentiated within 48 h. We next substituted purified fetal bovine serum albumin (16.6 g/L, Fisher Scientific) for the serum replacement to determine whether albumin caused the differentiation. This medium allowed hESCs to maintain an undifferentiated morphology for about 7 days; however, the cells had a reduced proliferation rate and eventually differentiated into a mixed population of cells. These results suggest that components other than albumin contained in the serum replacement are responsible for the rapid differentiation of UM-cultured cells. CM reduces this differentiation-inducing activity, but also provides positive factors to sustain hESC self-renewal. In addition to albumin, serum replacement also contains other components that are required for hESC culture, so serum replacement rather than albumin was used in all subsequent studies.

To examine whether the differentiation-inducing activity in UM stimulates BMP signaling in hESCs, we assessed by western blotting the level of phosphorylated Smad1, an immediate effector downstream of BMP receptors. Smad1 phosphorylation (the antibody used here could also detect phosphorylation of other BMP effectors Smad5 and -8) was low in H1 cells cultured in CM, but was high in cells cultured for 24 h in UM, or in CM+BMP4. The addition of noggin to UM reduced the level of Smad1 phosphorylation, but the addition of 40 ng/ml bFGF to UM left the level of Smad1 phosphorylation unchanged. BMP signaling can induce expression of BMP ligands, forming a positive feedback loop in cells from various species, including hESCs. BMP2/4 proteins were, indeed, detected at an increased level in UM-cultured hESCs compared to cells cultured in CM or in UM plus noggin. It is at present unclear whether there are BMPs in UM that directly stimulate BMP signaling in hESCs, or other differentiation-inducing molecules that indirectly stimulate BMP signaling by inducing BMP secretion. Noggin and another BMP antagonist gremlin were both detected in medium conditioned by the fibroblast. These data demonstrate that an elevated, but repressible, BMP signaling activity is present in UM-cultured hESCs, and that both BMP agonists and antagonists are present in fibroblast-supported culture of hESCs.

We further assessed BMP signaling in hESCs (H14) cultured in various media in the presence or absence of protein factors, by using a luciferase reporter plasmid specifically responsive to BMP/Smads. The reporter activity increased with an increasing concentration of the serum replacement or BMP4, and decreased with an increasing concentration of noggin or bFGF. 500 ng/ml Noggin and 40 ng/ml bFGF had synergistic effect in reducing the reporter activity to the level similar to that achieved by CM. Somewhat surprisingly, even higher levels of bFGF (100 ng/ml) reduced BMP signaling to a level comparable to that found in CM without the addition of noggin. These results suggest that serum replacement indeed contains BMP-like activity, which can be reduced by noggin and/or bFGF.

The Id1 promoter contains BMP responsive elements, and Id1 was previously shown to be a target of BMP4 signaling in both human and mouse ESCs. We therefore examined the expression of Id genes as a second indicator of BMP signaling activity in hESCs cultured in various media. Id1-4 transcripts were higher in hESCs (H9) cultured for 24 h in UM or CM+BMP4 than in cells cultured in CM, and addition of noggin to UM reduced expression of the Id genes.

UM/bFGF/noggin sustains undifferentiated proliferation of hESCs. UM supplemented with 0.5 µg/ml noggin and 40 ng/ml bFGF sustained undifferentiated proliferation of hESCs. H1 cells were plated at an equal number and cultured for 7 days in CM, UM, UM plus bFGF, UM plus noggin, or UM plus bFGF and noggin. Oct4$^+$ cell numbers were significantly higher after 7 days in CM and UM/bFGF/noggin than in UM, UM/bFGF, or UM/noggin. Intermediate Oct4$^+$ cell numbers were detected in UM/bFGF and UM/noggin, suggesting a synergistic effect between noggin and bFGF. hESCs cultured in UM/bFGF or UM/noggin could be propagated for multiple passages, but differentiated cells accumulated in either the middle (in UM/bFGF) or edge (in UM/noggin) of the hESC colonies. Increased differentiation also occurred in cells cultured in UM/bFGF/noggin if the noggin concentration was reduced to 0.1 µg/ml and the bFGF concentration was reduced to 10 ng/ml. The noggin in UM/bFGF/noggin could be substituted by gremlin (5 µg/ml) or a soluble BMP receptor IA (0.5 µg/ml) (data not shown), supporting that noggin's effects are indeed through the interruption of BMP receptor activation by BMPs.

Three different HESC lines (H1, H9, and H14) that had been expanded in UM/bFGF/noggin for more than 40 days (7, 6, and 6 passages, respectively) remained positive for Oct4, but subsequently differentiated if switched to UM lacking bFGF and noggin. UM/bFGF/noggin-cultured hESCs continued to express other ES cell markers, including Nanog and Rex1, and the cell surface markers SSEA4 and TRA-1-60 (data not shown). Even in the best cultures, hESCs are mixed with a small percentage of spontaneously differentiated cells. For example, low levels of the trophoblast marker chorionic gonadotropin β-subunit (CGβ) can be detected in CM-cultured ES cells, indicating the existence of small populations of trophoblast. This marker, however, was not detectable in UM/bFGF/noggin-cultured cells. The neural progenitor markers Pax6 and NeuroD1, the mesodermal marker brachyury, and the endodermal marker HNF3α were all negative in CM- and UM/bFGF/noggin-cultured hESCs. Thus, ES cells propagated in UM/bFGF/noggin maintained characteristic ES cell markers following extended culture.

We further examined hESCs after long-term culture in UM/bFGF/noggin. H9 cells were continuously cultured in UM/bFGF/noggin for 32 passages. H1 and H14 cells cultured in UM/bFGF/noggin were frozen after passages 20 and 16, respectively. H14 cells were subsequently thawed directly into UM/bFGF/noggin and cultured to passage 18. The population doubling time and percentage of Oct4⁺ cells of both H9 and H14 cells cultured in UM/bFGF/noggin for 27 and 18 passages, respectively, were similar to those for CM-cultured control hESCs.

UM/bFGF/noggin maintains the developmental potential of hESCs. When treated with BMP4 in CM for 3-7 days, hESCs that had been previously cultured in UM/bFGF/noggin for 10 passages differentiated into a flattened epithelium and secreted human chorionic gonadotropin (HCG) into the medium, indicating trophoblast differentiation. Embryoid bodies (EBs) derived from H1 cells cultured in UM/bFGF/noggin for 5 passages, and from control CM-cultured cells, expressed the trophoblast marker CGβ and markers of the three germ layers, including Pax6, NeuroD1, brachyury, and HNF3α. EB cells also had reduced expression of the ES cell markers Oct4, Nanog, and Rex1. H1 and H9 cells cultured in UM/bFGF/noggin for 7 and 6 passages, respectively, were injected into SCID-beige mice. Teratomas exhibiting complex differentiation developed in the mice 5-6 weeks post-inoculation.

UM/bFGF/noggin-cultured ES cells are karyotypically normal. H1 cells cultured in UM/bFGF/noggin for 5 passages, H9 for 33 passages, and H14 for 19 passages were karyotyped by standard G-banding, and chromosomes 12 and 17 were examined by fluorescence in situ hybridization. The cells retained normal karyotypes.

ES cells cultured in defined and humanized system remain undifferentiated. Although replacement of the CM with UMFN has eliminated the need for mouse-derived feeder cells, the UM still contained fetal bovine serum-derived albumin extract—an incompletely defined component, and the plate-coating material Matrigel is a solubilized basement membrane matrix extracted from a mouse tumor. Thus, further removing these animal materials was thought to be appropriate to define a humanized culture system for human ES cells. We first searched for a defined and humanized serum replacement to substitute for the KNOCKOUT SR product previously used, and Sigma's 50× Seral Replacement 3 (SR3) which is composed of three human proteins: albumin, insulin, and transferrin was considered. It has been shown that laminin can substitute for Matrigel to coat plates for human ES cell culture in the CM. We then established a system where human ES cells were cultured on laminin-coated plates and in a UM containing 5×SR3 instead of KNOCKOUT SR, plus 40 ng/ml FGF2 and 0.5 μg/ml noggin. ES cells in this system also retained ES cell identity after multiple weekly passages. Therefore, this combination makes up a defined and humanized culture system suitable for human ES cells.

These sets of data, taken together, demonstrate that feeder cells and conditioned medium can be avoided by the use of culture conditions including a bone morphogenic protein antagonist, like noggin, together with an FGF. The other constituents of the culture medium can then be selected to avoid animal products. The result is a highly defined medium that permits the long term culture and proliferation of human embryonic stem cells while retaining all of the potential of those cells.

---

We claim:

1. A method for culturing human embryonic stem cells in a feeder independent culture, the method comprising the step of culturing the human embryonic stem cells in a medium including salts, vitamins, amino acids, glucose, a fibroblast growth factor and a bone morphogenetic protein antagonist in the presence of an extracellular matrix in sufficient amount to maintain the stem cells in an undifferentiated state wherein the bone morphogenetic protein antagonist is noggin.

2. The method of claim 1 wherein the medium includes thefibroblast growth factor in a concentration of at least 4 ng/ml.

3. The method of claim 1 wherein the fibroblast growth factor isbFGF at a concentration of 40 ng/ml.

4. In a method of culturing human embryonic stem cells in a medium including salts, vitamins, amino acids, and a fibroblast growth factor with extracellular matrix, the improvement comprising adding to the medium an amount of an antagonist of bone morphogenetic protein signaling in an amount sufficient to maintain the cells in an undifferentiated state without exposure of the stem cells or the medium to feeder cells wherein the bone morphogenetic protein antagonist is noggin.

5. An in vitro cell culture comprising in a culture vessel: human embryonic stem cells; an extracellular matrix; and a culture medium, the culture medium comprising salts, vitamins, amino acids, glucose, a fibroblast growth factor, and a bone morphogenetic protein signaling antagonist wherein the bone morphogenetic protein antagonist is noggin in sufficient amount to maintain the stem cells in an undifferentiated feeder independent state, the medium being free of feeder cells and never having been exposed to feeder cells.

6. The cell culture as claimed in claim 5 wherein the medium includes the fibroblast growth factor in a concentration of at least 4 ng/ml of bFGF.

7. The cell culture as claimed in claim 5 wherein the medium further comprises proteins selected from the group consisting of albumin, insulin and transferrin.

8. The cell culture as claimed in claim 7 wherein the proteins are human.

9. The cell culture as claimed in claim 7 wherein the proteins are recombinant proteins.

* * * * *

UNITED STATES PATENT AND TRADEMARK OFFICE
CERTIFICATE OF CORRECTION

PATENT NO. : 7,514,260 B2
APPLICATION NO. : 11/134564
DATED : April 7, 2009
INVENTOR(S) : Ren-He Xu and James A. Thomson Page 1 of 1

It is certified that error appears in the above-identified patent and that said Letters Patent is hereby corrected as shown below:

Column 20, line 58, claim 2, the term "thefibroblast" in the phrase "...thefibroblast growth factor in a concentration of at least 4..." is incorrect. When corrected, the term --the fibroblast-- should be inserted in the phrase as follows: --...the fibroblast growth factor in a concentration of at least 4...--

Column 20, line 61, claim 3, the term "isbFGF" in the phrase "...factor isbFGF at a concentration of 40ng/ml." is incorrect. When corrected, the term --is bFGF-- should be inserted in the phrase as follows: --...factor is bFGF at a concentration of 40ng/ml.--

Column 20, line 63, claim 4, the word "and" should be replaced by the word "with" in the phrase "...a medium including salts, vitamins, amino acids, and a fibro-..." When corrected, the phrase should read as follows: --...a medium including salts, vitamins, amino acids, with a fibro-...--

Signed and Sealed this

Twenty-sixth Day of May, 2009

JOHN DOLL
*Acting Director of the United States Patent and Trademark Office*